United States Patent
Kim et al.

(10) Patent No.: US 11,109,955 B2
(45) Date of Patent: Sep. 7, 2021

(54) DERMAL LAYER FOR GRAFTING HAVING IMPROVED GRAFT SURVIVAL RATE AND METHOD FOR PRODUCING SAME

(71) Applicant: PHARMARESEARCH PRODUCTS CO., LTD., Gangneung-si (KR)

(72) Inventors: Ik Soo Kim, Seongnam-si (KR); Han Gyu Kim, Wonju-si (KR); Su Yeon Lee, Seongnam-si (KR)

(73) Assignee: PHARMARESEARCH CO., LTD., Gangneung-si (KR)

( * ) Notice: Subject to any disclaimer, the term of this patent is extended or adjusted under 35 U.S.C. 154(b) by 13 days.

(21) Appl. No.: 16/331,226

(22) PCT Filed: Mar. 22, 2017

(86) PCT No.: PCT/KR2017/003070
§ 371 (c)(1),
(2) Date: Mar. 7, 2019

(87) PCT Pub. No.: WO2018/048047
PCT Pub. Date: Mar. 15, 2018

(65) Prior Publication Data
US 2019/0274816 A1    Sep. 12, 2019

(30) Foreign Application Priority Data
Sep. 7, 2016 (KR) .................. 10-2016-0114733

(51) Int. Cl.
*A61F 2/10* (2006.01)
*A61L 27/50* (2006.01)
(Continued)

(52) U.S. Cl.
CPC ............... *A61F 2/105* (2013.01); *A61F 2/10* (2013.01); *A61L 27/20* (2013.01); *A61L 27/36* (2013.01);
(Continued)

(58) Field of Classification Search
CPC combination set(s) only.
See application file for complete search history.

(56) References Cited

U.S. PATENT DOCUMENTS 9,532,866 B2    1/2017   Kim et al.
2004/0031067 A1  2/2004   Herlyn et al.
(Continued)

FOREIGN PATENT DOCUMENTS

CN    104203285 A    12/2014
JP    2013-530729 A   8/2013
(Continued)

OTHER PUBLICATIONS

Guo et al. "Enhanced angiogenesis of gene-activated dermal equivalent for treatment of full thickness incisional wounds in a porcine model" Biomaterials 31 (2010) 7308-7320. (Year: 2010).*
(Continued)

*Primary Examiner* — Marcia S Noble
*Assistant Examiner* — Lauren K Van Buren
(74) *Attorney, Agent, or Firm* — Rothwell, Figg, Ernst & Manbeck, P.C.

(57) ABSTRACT

The present invention relates to a dermal layer which is for grafting and has an improved graft survival rate, and a method for producing the same, wherein the dermal layer for grafting can be produced by filling a filling solution, including a DNA fragment mixture and chitosan, into an acellular dermal matrix from which cells have been removed. It was observed that the dermal layer for grafting produced in this manner, due to the filling solution filled therein and including a DNA fragment mixture and chitosan, increases the rate at which cells flow in from the tissue surrounding the graft and are fixed, and thereby alleviates an initial inflammatory reaction and promotes blending with the surrounding tissue.

15 Claims, 3 Drawing Sheets

(51) Int. Cl.
*A61L 27/40* (2006.01)
*A61P 7/02* (2006.01)
*A61L 27/36* (2006.01)
*A61L 27/60* (2006.01)
*A61L 27/20* (2006.01)

(52) U.S. Cl.
CPC .......... *A61L 27/3633* (2013.01); *A61L 27/60* (2013.01); *A61L 27/362* (2013.01); *A61L 2430/40* (2013.01)

(56) References Cited

U.S. PATENT DOCUMENTS

| | | | |
|---|---|---|---|
| 2010/0056462 A1 | 3/2010 | Kanatani et al. | |
| 2010/0266559 A1 | 10/2010 | Nataraj et al. | |
| 2011/0172293 A1* | 7/2011 | Fish | A61K 31/7088 514/44 A |
| 2013/0210675 A1* | 8/2013 | Guo | C08H 1/06 506/16 |
| 2013/0274190 A1* | 10/2013 | Wang | A61L 15/425 514/9.4 |
| 2014/0296623 A1 | 10/2014 | Owens et al. | |
| 2014/0341870 A1 | 11/2014 | Isaev et al. | |

FOREIGN PATENT DOCUMENTS

| | | | |
|---|---|---|---|
| JP | 2016-064141 A | 4/2016 | |
| KR | 10-0469661 B1 | 2/2005 | |
| KR | 10-2008-0011286 A | 2/2008 | |
| KR | 10-1362402 B1 | 2/2014 | |
| KR | 10-1710615 B1 | 2/2017 | |
| WO | 2014-046744 A1 | 3/2014 | |
| WO | WO-2015125117 A1 * | 8/2015 | ............. A61L 27/52 |

OTHER PUBLICATIONS

Lu "Porous Chitosan Scaffolds with Embedded Hyaluronic Acid/Chitosan/Plasmid DNA nanoparticles encoding TGF-Beta induces DNA Controlled Release, Transfected Chondrocytes, and Promoted Cell Proliferation" Plus One Jul. 2013, vol. 8, Issue 7. (Year: 2013).*

Search Report issued for European Patent Application No. 17848932.4 dated Mar. 27, 2020, 7 pages.

Guo et al., "Enhanced Angiogenesis of Gene-Activated Dermal Equivalent for Treatment of Full Thickness Incisional Wounds in a Porcine Model" Biomaterials 31 (2010) 7308-7320.

International Search Report and Written Opinion issued for International Application No. PCT/KR2017/003070 dated Jul. 7, 2017, 8 pages.

* cited by examiner (A) Control 1: Acellular dermal matrix immersed in PBS solution (B) Control 2: Acellular dermal matrix immersed in loading solution 1-1

(C) Dermal layer for grafting of the present invention: Acellular dermal matrix loaded with loading solution 1-1

(A) Control 1: Acellular dermal matrix immersed in PBS solution (B) Control 2: Acellular dermal matrix immersed in loading solution 1-1

(C) Control 3: Acellular dermal matrix loaded with 0.005 % by weight chitosan (D) Dermal layer for grafting of the present invention: Acellular dermal matrix loaded with loading solution 1-1

(A) Control 1: Acellular dermal matrix immersed in PBS solution (B) Dermal layer for grafting of the present invention: Acellular dermal matrix loaded with loading solution 1-1

(A) Control 1: Acellular dermal matrix immersed in PBS solution (B) Dermal layer for grafting of the present invention: Acellular dermal matrix loaded with loading solution 1-1

DERMAL LAYER FOR GRAFTING HAVING IMPROVED GRAFT SURVIVAL RATE AND METHOD FOR PRODUCING SAME

CROSS-REFERENCE TO RELATED APPLICATIONS

The application is a 35 U.S.C. § 371 National Phase Entry Application from PCT/KR2017/003070, filed on Mar. 22, 2017, which claims the benefit of Korean Patent Application No. 10-2016-0114733 filed on Sep. 7, 2016, the disclosures of which are incorporated herein in their entirety by reference.

TECHNICAL FIELD

The present invention relates to a dermal layer for grafting having an improved graft survival rate and a production method therefor. More particularly, the present invention relates to a dermal layer for grafting which is improved in graft survival rate upon grafting of a biologically inactive dermal layer loaded with a loading solution containing a DNA fragment mixture and chitosan.

BACKGROUND ART

Skin is the largest organ, covering the entire human body and has functions of preventing the loss of body fluid and the influx of toxic substances and microbes from the outside and protecting the body from physical stimuli, radiation, UV light, etc. Skin is an important complex organ containing various appendages inclusive of hair follicles, hairs, sweat glands, sebaceous glands, etc., performing various functions in addition to a protecting membrane function (KIM Chun-Ho, et al., 2002). Skin is largely composed of three primary layers: the epidermis, the dermis, and the hypodermis (subcutaneous tissue).

The epidermis is the outermost thin layer of the skin and consists of newly differentiating cells that protect the skin from the outside environment and which are continuously replaced with new cells. The epidermis is stratified into the stratum basalis (basal cell layer), the stratum spinosum (spinous cell layer), the stratum granulosum (granular cell layer), and the stratum corneum in the order from bottom to top. Many stacked layers of dead cells in the outermost portion of the skin serve as a protective membrane.

The dermis is the layer of skin beneath the epidermis that provides matrices supporting various structures such as blood vessels, nerves, etc. The epidermis is composed of collagen, elastic fibers, and extracellular matrix. The epidermis is generally divided into two areas: the papillary layer as a superficial area that is rich in fibroblasts and has microvessels distributed therein; and the reticular connective tissue as a deep region rich in collagenous fiber.

The hypodermis, which lies between the dermis and the muscle and bone, consists of adipose tissues and connective tissues and harbors blood vessels, lymphatic vessels, and nerve endings. The adipose tissue in the hypodermis provides protection from outside pressure and a padding effect against friction, thereby making easy the movement of the skin on the deep structures such as bones and muscles. In addition, the plentiful adipose tissue absorbs impact to protect the body and accumulate excess nutrients therein as well as generating heat and retaining the generated heat therein.

The skin may be impaired in part by burning, trauma, dermal diseases, etc. In order to cure or reconstruct the impaired region, an autograft, which is a tissue transferred from one spot to another on the patient's body, a homograft (allograft), which is a tissue transferred from one person to another, or a heterograft (xenograft), which is tissue taken from a species different from the patient, may be transplanted to the damaged region. Of them, an autograft is the most ideal, but is restricted in terms of the source from which skin tissue can be obtained when the impaired area is extensive. In addition, the harvesting region leaves a new scar. An allograft serves, rather than being permanently engrafted, to help the movement of cells at the periphery of the impaired region and heal the impaired region.

For a patient suffering from severe skin loss, a scaffold capable of covering the impaired region is required. In this regard, artificial skin has been developed. Artificial skin must function as a protective membrane preventing infection and body fluid loss at the impaired region and fundamentally block significant dermal shrinkage that may occur during a healing procedure without leaving a scar at the impaired region of the patient (Yannas I. V., 1995).

Artificial skin may be generally divided into two skin substitutes: a temporary skin equivalent for use as a wound dressing; and a permanent skin equivalent for cultured skin or in vivo implantation. The temporary skin equivalent is used to temporarily protect a skin wound caused by burning or trauma until recovery of the skin from the injury, playing a role in preventing fluid release from the body, absorbing an exudate, and protecting the body against microbial invasion and infection. On the other hand, the permanent skin equivalent is composed of a synthetic polymer and a natural polymer and functions to provide a passage through which body cells easily penetrate into the impaired region and actively help the cells regenerate into the original skin tissue as well as serving as a wound dressing. The permanent skin equivalent itself is degraded and absorbed in the human body. Bioartificial skin, which is a kind of permanent artificial equivalent to skin, provides growth factors and extracellular matrices necessary for the regeneration of impaired tissues as well as serving as a protective membrane and has proven to have excellent effects such as rapid wound healing and scar reduction. Now, bioartificial skin is clinically applied to the treatment of burns, pressure sores, traumas, intractable ulcers, diabetic skin necrosis, pressure erosion, etc. and to plastic surgery.

The success of skin transplantation varies depending on the thickness of explants to be grafted and the management of graft sites (Gallico G. G. 3rd., 1990; Kunert P., 1991). For successful skin transplantation, active research has been made into the mechanism of skin transplantation, skill development, post-surgical management of donating sites, management of surgical sites, etc. (Johnson C. S., et al, 2001; McDowell F., 1977). With regard to the generally known mechanism of skin grafting, the graft survives when being supplied with a blood stream from the implantation medium and the successful outcome of a skin graft is determined by plasmatic imbibition and revascularization, which are diffusion effects of nutrients and oxygen occurring within 24-48 hours (Johnson C. S., et al., 2001). The most common failure factor is hematoma under the graft or fluid collection and infection is positioned as the second most common cause (Barret J. P., et al, 2002; McGergor A. D., et al., 2000). There might be a variety of other factors affecting successful outcomes of skin grafting, but there are insufficient research results about such factors and no controllable and suitable preconditions or references for a skin graft have been suggested thus far (A N Ki-Chan et. al., 2012).

Chitosan (poly (β-(1→4)-2-amino-2-deoxy-D-glucan), which is a natural linear polysaccharide composed of β-(1→4)-linked D-glucosamine, is produced by deacetylation of the acetamide group at position C2 on chitin (poly (β-(1→4)-2-acetamined-2-deoxy-D-glucan). Chitosan is of lower crystallinity than chitin and is dissolved in an aqueous diluted solution of an inorganic acid such as hydrochloric acid, sulfuric acid, etc., an organic acid such as formic acid, acetic acid, propionic acid, oxalic acid, succinic acid, etc., an oxy acid such as gluconic acid, lactic acid, malic acid, etc., or an acidic amino acid such as glutamic acid while forming an acid salt (Mussarelli R. A. A., 1997; Brine C. J., et al., 1992).

A chitosan solution is characterized by high viscosity and varies in viscosity depending on deacetylation, ionic strength, pH, temperature, etc. For example, the viscosity of a chitosan solution decreases with decreasing pH therein and increases with increasing pH therein. In contrast, the viscosity of a chitosan solution decreases with the elevation of temperature and returns back again when the initial temperature is attained.

Chitosan has a biological activity for animals including humans and for plants, finding applications and uses in a variety of fields. Among the biological activities of chitosan, an antibacterial activity is the most widely applied. The antibacterial activity is known to be exerted by cationized amino groups on chitosan. An ionic bond occurs between the cationized amino acid group of chitosan and the acidic groups such as sialic acid, phospholipids, etc. in the bacterial cell wall to form a polyelectrolyte complex. Thus, the resultant polarization of phospholipids of the cell membrane ruptures the cell membrane organization of the side opposite to the contact point to leak cytoplasmic materials from the cells, resulting in cell death. In addition, chitosan has been continually studied for use as a polymer material having excellent compatibility to the human body and minimal rejection in the biomedical engineering field, arising as body-compatible biopolymer materials such as wound dressings, wound ointments, dental materials, orthopedic materials, surgical sutures, etc. (K O, Byoung Yol et al., 2002).

Leading to the present invention, intensive and thorough research, conducted by the present inventors, into a composition for skin graft resulted in the finding that a dermis layer for grafting prepared by loading a biologically inactive dermis layer with a loading solution containing a DNA fragment mixture and chitosan exhibits an improved graft survival rate in the engraftment site.

As prior arts, Korean Patent Nos. 0469661 and 1362402 are similar to the present invention in terms of acellular dermal layer for grafting, but there is a configurational difference therebetween in that the former does not discloses a method of loading a loading solution containing a DNA fragment mixture and chitosan. In addition, US Patent No. 20040031067 A discloses a method of injecting a nucleic acid coding for a growth factor upon skin grafting, but describes neither chitosan at all, nor a drug-loaded dermal composition, which makes a difference from the configuration of the present invention. Korean Patent No. 1534276 is configurationally similar to the present invention with respect to the composition that comprises polydeoxyribonucletides for improving a graft survival rate of adipocytes after transplantation of fat, but differs from the present invention in that the former states neither chitosan nor a drug-loaded dermal composition.

DETAILED DESCRIPTION OF THE INVENTION

Technical Problem

The purpose of the present invention is to provide a dermal layer for grafting that is improved in graft survival rate and a method for producing the same.

Technical Solution

The present invention relates to a method for producing a dermal layer for grafting, comprising: a first step of preparing a DNA fragment mixture stock solution; a second step of preparing a chitosan stock solution; a third step of mixing the DNA fragment mixture stock solution and the chitosan stock solution and stirring the resulting mixture, followed by sterilization to afford a loading solution containing the DNA fragment mixture and chitosan; and a fourth step of loading the loading solution to an acellular dermal matrix.

The producing method may comprise: a first step of dissolving a DNA fragment mixture in a buffer at 50° C. to 70° C. for 1 to 3 hours while stirring to give a DNA fragment stock solution; a second step of dissolving chitosan in an acidic buffer to give a chitosan stock solution; a third step of mixing the DNA fragment stock solution and the chitosan stock solution at a weight ratio of 20:1-10,000:1 of the DNA fragment mixture: the chitosan and stirring the resulting mixture at 65° C. to 75° C. for 1 to 2 hours, followed by sterilization to afford a loading solution containing the DNA fragment mixture and chitosan; and a fourth step of loading the loading solution to an acellular dermal matrix by means of a vacuum drug loading device.

The DNA fragment mixture may be isolated from fish testis or sperm.

The fish may be of the family Salmonidae.

The DNA fragment mixture may have a molecular weight of 50 kDa to 10,000 kDa.

The DNA fragment mixture may be present in an amount of 0.01% by weight to 3% by weight, based on the total weight of the loading solution.

The chitosan may have a molecular weight of 3 kDa to 1,000 kDa.

The chitosan may be used in an amount of $1\times10^{-6}$% by weight to 0.15% by weight, based on the total weight of the loading solution.

The acellular dermal matrix in the fourth step may be a biologically inactivated collagen-based tissue supplement material that has been obtained by removing cells and impurities from a dermal matrix and subjecting the dermal matrix to virus inactivation and then to lyophilization.

The dermal matrix may be an autograft, allograft, or heterograft.

The loading in the fourth step may be carried by introducing the viscous loading solution into the acellular dermal matrix by means of a pressure to fill empty spaces between collagens.

The vacuum drug loading device is designed to be loaded with the loading solution in one direction and generate a positive or negative pressure to infiltrate the loading solution into empty spaces between collagens inside the acellular dermal matrix.

In addition, the present invention relates to a dermal layer for grafting, produced by the production method.

Also, the present invention relates to an agent for treating skin injury, comprising the dermal layer for grafting.

The skin injury may be caused by at least one selected from the group consisting of abrasion, incision, laceration, skin avulsion, skin bruise, puncture wound, and surgical skin excision.

Below, a detailed description will be given of the present invention.

The present invention relates to a method for producing a dermal layer for grafting, comprising: a first step of preparing a DNA fragment mixture stock solution; a second step of preparing a chitosan stock solution; a third step of mixing the DNA fragment mixture stock solution and the chitosan stock solution and stirring the resulting mixture, followed by sterilization to afford a loading solution containing the DNA fragment mixture and chitosan; and a fourth step of loading the loading solution to an acellular dermal matrix.

The producing method may comprise: a first step of dissolving a DNA fragment mixture in a buffer at 50° C. to 70° C. for 1 to 3 hours while stirring to give a DNA fragment stock solution; a second step of dissolving chitosan in an acidic buffer to give a chitosan stock solution; a third step of mixing the DNA fragment stock solution and the chitosan stock solution at a weight ratio of 20:1-10,000:1 of the DNA fragment mixture: the chitosan and stirring the resulting mixture at 65° C. to 75° C. for 1 to 2 hours, followed by sterilization to afford a loading solution containing the DNA fragment mixture and chitosan; and a fourth step of loading the loading solution to an acellular dermal matrix by means of a vacuum drug loading device.

Examples of the buffer available for the preparation of the DNA fragment stock solution in the first step include, but are not limited to, sodium phosphate dibasic dodecahydrate, sodium chloride, magnesium chloride, potassium chloride, phosphate buffered saline, HEPES (N-(2-hydroxyethyl)-piperazine-N'-2-ethanesulfonic acid), and glycerol-3-phosphate buffer, with preference for sodium phosphate dibasic dodecahydrate.

The DNA fragment mixture may be isolated from fish testis or sperm.

The fish may be of the family Salmonidae and may be preferably salmon or trout and most preferably salmon.

The term "DNA fragment mixture" refers to a mixture in which the biopolymer DNA, consisting of phosphate, 4 kinds of bases, and deoxyribose, exists as mixed fragments of reduced molecular weights.

The DNA fragment mixture is a mixture of DNA fragments of particular sizes, which exerts a pharmaceutical effect or serves as a polymeric scaffold.

The DNA fragment mixture may be a polydeoxyribonucleotide and a polynucleotide.

The polydeoxyribonucleotide is known as a material that plays a role in cell regeneration and wound healing and the polynucleotide may serve as a scaffold structure to configure a cell regeneration environment.

The DNA fragment mixture may range in molecular weight from 50 kDa to 10,000 kDa, preferably from 50 kDa to 5,000 kDa, and most preferably from 50 kDa to 3,500 kDa.

Examples of the acidic buffer solution available for the preparation of the chitosan stock solution in the second step include, but are not limited to, acetic acid, hydrochloric acid, ascorbic acid, lactic acid, and nitric acid, with preference for acetic acid.

The chitosan may have a molecular weight of 3 kDa to 1,000 kDa.

In the third step, the weight ratio between the DNA fragment mixture and the chitosan may be 20:1-10,000:1, preferably 20:1-1,000:1, and more preferably 50:1-200:1.

The DNA fragment mixture may be used in an amount of 0.01% by weight to 3% by weight, based on the total weight of the loading solution, preferably in an amount of 0.1% by weight to 2% by weight, and most preferably in an amount of 0.5% by weight to 1.5% by weight. It is difficult to expect an effect of improving a graft survival rate for less than 0.01% by weight of the DNA fragment mixture. Greater than 3% by weight of the DNA fragment mixture may incur a problem in the procedure of producing the loading solution.

The chitosan may be used in an amount of $1 \times 10^{-6}$% by weight to 0.15% by weight, based on the total weight of the loading solution, preferably in an amount of $1 \times 10^{-5}$% by weight to 0.15% by weight, and most preferably in an amount of $1 \times 10^{-4}$% by weight to 0.075% by weight. When chitosan is used in an amount less than $1 \times 10^{-6}$% by weight or greater than 0.15% by weight, the acellular dermal matrix is filled at a low rate because of the viscosity of the loading solution.

The chitosan may be mixed with the DNA fragment mixture to increase the viscosity of the loading solution. This viscosity increase leads to an increase of loading efficiency at which the loading solution occupies empty spaces between collagens within the acellular dermal matrix, so that the DNA fragment mixture introduced into the acellular dermal matrix can exist inside the matrix.

The chitosan can increase the loading efficiency of the loading solution through the formation of ionic bonds with collagen, which is the negatively charged main ingredient of the acellular dermal matrix.

The sterilization in the third step may be achieved by, but not limited to, autoclaving, dry heat sterilization, ethylene oxide (EO) gas sterilization, etc., and preferably by autoclaving.

The acellular dermal matrix in the fourth step is a biologically inactive collagen-based tissue supplement material and scaffold that has been obtained by removing cells and impurities from a dermal matrix and subjecting the dermal matrix to virus inactivation and then to lyophilization.

The supplement material may be adapted to cover a wound and may be artificial skin.

The acellular dermal matrix may be prepared from a dermal matrix through a series of processes or may be a commercially available product.

The dermal matrix may be an autograft, an allograft, or a heterograft.

The loading in the fourth step is intended to introduce the viscous loading solution into the acellular dermal matrix by means of a pressure to fill empty spaces between collagens, so that a large amount of the effective ingredients exists inside the graft. Particularly when the loading solution is difficult to introduce into the acellular dermal matrix due to the viscosity thereof, a negative or positive pressure may be applied to promote the entry of the loading solution into the acellular dermal matrix, thereby increasing the efficiency of filling empty spaces between collagens. In addition, the promoted entry of the loading solution into the matrix induces an increase in the contact area between the materials contained in the loading solution and the main ingredient collagen of the acellular dermal matrix and provides an increased opportunity of ionic bond formation therebetween, thereby increasing loading efficiency.

The loading may be achieved by means of a vacuum drug loading device.

The vacuum drug loading device may be a device that is designed to apply a positive or negative pressure to the acellular dermal matrix to allow the entry of the loading solution into the acellular dermal matrix. Preferably, a negative pressure is employed.

The vacuum drug loading device may include a portion for fixing an acellular dermal matrix thereto, a portion into which a loading solution is introduced, and a portion to which a vacuum pump for providing a positive or negative pressure is connected.

The fixing portion must be packed in order to prevent the leakage of drugs by the pressure upon drug loading.

In addition, the present invention relates to a dermal layer for grafting, produced by the production method.

The dermal layer for grafting, loaded with the loading solution containing the DNA fragment mixture and chitosan, can be improved in graft survival rate as the loading solution promotes the migration of cells from tissues adjacent to the graft site and the fusion of the dermal layer to the adjacent tissues. Thanks to the effect, in addition, the dermal layer can alleviate initial inflammation and bring about a fast recovery after implantation.

Further, the present invention relates to an agent for treating skin injury, the agent comprising the dermal layer for grafting.

The skin injury may be caused by at least one selected from the group consisting of abrasion, incision, laceration, skin avulsion, skin bruise, puncture wound, and surgical skin excision.

The treatment of skin injury may be carried out by grafting a supplement material or a scaffold onto a seriously injured skin site to cover the wound region and to prevent the loss of body fluid without leaving a scar on the wound site.

Advantageous Effects

The present invention relates to a dermal layer for grafting having an improved graft survival rate and a method for producing the same. The dermal layer may be produced by loading a biologically inactive dermal matrix with a loading solution containing a DNA fragment mixture and chitosan. The dermal layer for grafting thus produced was found to reduce initial inflammation and fuse fast to adjacent tissues as the loading solution containing the DNA fragment mixture and chitosan, loaded into the dermal layer, promotes the inflow and fixation of cells of tissues adjacent to the grafted site to the dermal layer.

Therefore, when grafted on an injured skin region, the dermal layer for grafting of the present invention is expected to exhibit an improved graft survival rate and a rapid therapeutic effect on skin injury.

MODE FOR CARRYING OUT THE INVENTION

Figure 1:
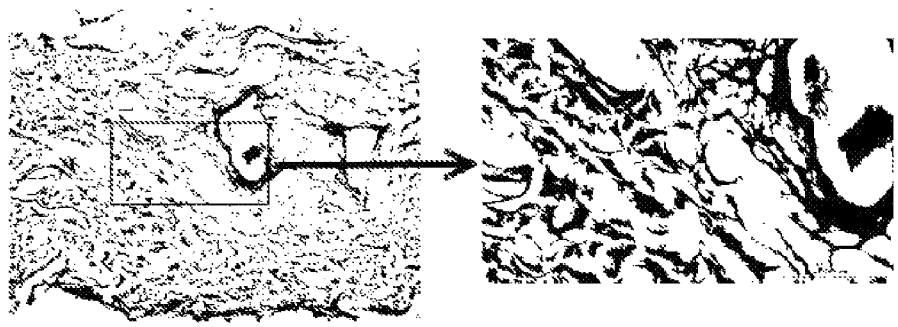
FIG. 1 shows results determining whether or not a loading solution containing a DNA fragment mixture and chitosan is loaded. No violet regions stained by hematoxylin are found in either control 1, which is an acellular dermal matrix not loaded with a loading solution (A), or control 2, which is an acellular dermal matrix immersed in a loading solution (B) whereas multiple portions stained violet are observed among red stains of collagens in the dermal layer for grafting according to the present invention (C). Black arrows indicate regions which are stained violet by hematoxylin and into which the loading solution is loaded.
Figure 1:
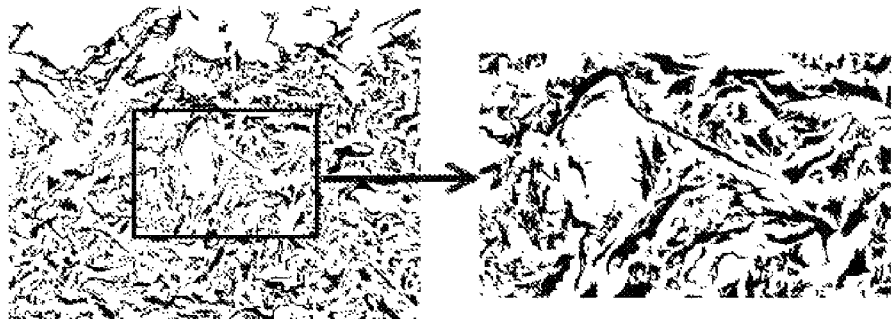
Figure 1:
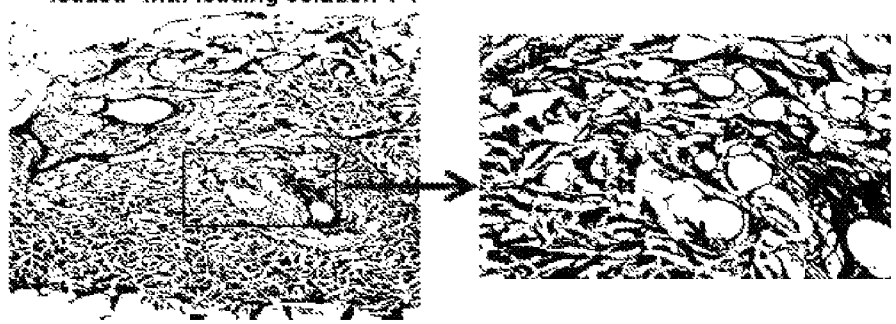

Hereinafter, particular embodiments of the present invention will be concretely explained. However, the present invention is not limited to the Examples given below, but can be embodied in other forms. Rather, they are provided to make the contents introduced herein thorough and perfect and to deliver the spirit of the present invention sufficiently.

Example 1: Production of Dermal Layer for Grafting Having Improved Graft Survival Rate Example 1-1. Preparation of Loading Solution Containing DNA Fragment Mixture and Chitosan For use in producing a dermal layer for grafting having an improved graft survival rate according to the present invention, a loading solution containing a DNA fragment mixture and chitosan was prepared.

A DNA fragment mixture was dissolved at 60° C. for 2 hours or longer in a 190 mM sodium phosphate dibasic dodecahydrate buffer with the aid of a heat stirrer to give a DNA fragment stock solution. Chitosan was dissolved at room temperature for 3 hours or longer in 90 mM acetic acid to give a chitosan stock solution.

The DNA fragment stock solution and the chitosan stock solution prepared above were mixed with each other and stirred for 2 hours at 70° C. in a heat stirrer. In this regard, the DNA fragment mixture and the chitosan were mixed according to the conditions given for the concentration and mix ratio in Table 1, below. The loading solution containing the DNA fragment mixture and chitosan thus prepared were sterilized using an autoclave.

TABLE 1

| Configuration | Final Concentration (% by weight) | | Mixture Ratio (weight ratio) | |
|---|---|---|---|---|
| | DNA fragment mixture | Chitosan | DNA fragment mixture | Chitosan |
| Loading solution 1-1 | 0.5 | 0.005 | 100 | 1 |
| Loading solution 1-2 | 0.01 | 0.0005 | 20 | 1 |
| Loading solution 1-3 | 0.01 | 0.000001 | 10000 | 1 |

TABLE 1-continued

| Configuration | Final Concentration (% by weight) | | Mixture Ratio (weight ratio) | |
|---|---|---|---|---|
| | DNA fragment mixture | Chitosan | DNA fragment mixture | Chitosan |
| Loading solution 1-4 | 3 | 0.15 | 20 | 1 |
| Loading solution 1-5 | 3 | 0.0003 | 10000 | 1 |

Example 1-2: Production of Dermal Layer for Grafting Having Graft Survival Rate

For use in producing a dermal layer for grafting having an improved graft survival rate according to the present invention, an acellular dermal matrix (tradename: Nature-Derma) was purchased from HansBiomed (Seoul, Korea). The commercial product is a collagen-based tissue supplement material that is prepared by removing cells and impurities from swine dermis through chemical treatment processes and inactivating viruses, followed by lyophilization and which is used for compensating for defected or injured bones, cartilages, etc. upon treatment in internal medicine or surgery or upon operation.

After the acellular dermal matrix purchased from Hans-Biomed was immobilized to a vacuum drug loading device, loading solution 1-1 was loaded to the acellular dermal matrix to produce a dermal layer for grafting according to the present invention. Loading solution 1-1 was identified to exhibit the best sense of use among the loading solutions comprising DNA fragment mixtures and chitosan, prepared in Example 1-1, as measured by inventor's inspection with the naked eye and a loading test.

Example 2: Identification of Loading of Loading Solution Containing DNA Fragment Mixture and Chitosan H&E (hematoxylin and eosin) staining was conducted to determine whether the acellular dermal matrix was loaded with a loading solution containing a DNA fragment mixture and chitosan. In the H&E staining procedure, hematoxylin binds to negatively charged nucleic acids to express a violet color while a red color appears as eosin binds to positively charged intracellular proteins. Collagen, which is the main ingredient of the acellular dermal matrix, is bound with eosin and stained red.

Among the dermal layers for grafting prepared in Example 1-2, the dermal layer loaded with loading solution 1-1 of Table 1 was subjected to H&E staining. In this regard, H&E staining was also conducted on controls including an acellular dermal matrix that was not loaded with a loading solution (control 1), and an acellular dermal matrix immersed for about one hour in a loading solution (control 2). The results are shown in FIG. 1.

As shown in FIG. 1, eosin stained collagen red in the acellular dermal matrix that had not been loaded with a loading solution containing a DNA fragment mixture and chitosan (control 1) (A) and the acellular dermal matrix immersed in loading solution (control 2) (B) whereas violet stains of hematoxylin were not observed in any of them. In contrast, violets stains (black arrows) were observed among the collagen stained red in the dermal layer for grafting, produced in Example 1-2 (C).

It is understood through the data that a loading solution cannot be introduced into the acellular dermal matrix by simple immersion in the loading solution. Therefore, it was recognized that a method using a vacuum drug loading device is most efficient as a method for loading an acellular dermal matrix with a loading solution containing DNA fragment mixture and chitosan.

Experimental Example 1: Preparation of Experimental Animal

For use in animal experiments, Sprague-Dawley lineage male rats, each being 7 weeks old and weighing 230-280 g, were purchased from YoungBio (Sungnam City, Korea). Solid diets for experimental animals were purchased (Harlan laboratories, Inc., USA) and placed in a feeder to which the experimental animals were given free access. Drinking water was filtered through a filter water flowing sterilizer and exposed to UV radiation before the animals were allowed to have free access to the drinking water in an automatic water feeder. A breeding chamber for the animals was maintained at a temperature of 23±3° C., a relative humidity of 55±15% under a light/dark cycle of 12/12 hours with a light intensity of 150~300 Lux.

Experimental Example 2: Identification of Graft Survival Rate of Dermal Layer for Grafting Experimental Example 2-1: Implantation of Dermal Layer for Grafting The dermal layer for grafting produced in Example 1-2 was immersed for an additional 30 min in the loading solution having the same concentration before use. An acellular dermal matrix that had not been loaded with a loading solution was immersed in PBS (phosphate buffer saline) (control 1) and in loading solution 1-1 for 30 min (control 2). An acellular dermal matrix was loaded with 0.005% by weight chitosan (control 3).

The rats in Experimental Example 1 were subjected to inhalation anesthesia with isoflurane and sterilized with povidone and ethanol at a back region to which a graft would be applied. After sterilization, the back region of the rat was incised along the spine and the epidermis was raised with forceps to secure an implantation space into which the dermal layer for grafting according to the present invention or the controls prepared above were then inserted, followed by suturing the incision. In this regard, one of the controls and the dermal layer for grafting according to the present invention were subcutaneously implanted into the left back and the right back with reference to the spine, respectively. Each of the rats that underwent surgery was placed in one cage and kept in a stable condition.

Experimental Example 2-2: Identification of Graft Survival Rate by Observation with Naked Eye After implantation in Experimental Example 2-1, the rats were sacrificed one by one each week. Tissues were separated from the grafted regions and monitored for a change in the dermal layer for grafting with the naked eye. The results are given in Table 2 and depicted in FIG. 2. Table 2 shows a change in the size of the dermal layer for grafting 4 weeks after implantation and expresses the post-implantation sizes in percentages (%) relative to the size of the dermal layer upon implantation.

TABLE 2

|  | Condition | Size of Dermal Layer for Grafting (%) |
| --- | --- | --- |
| Control 1 | Immersion in PBS | 100 |
| Control 2 | Immersion in loading solution 1-1 | 98 |
| Control 3 | Loaded with 0.005% by weight chitosan | 94 |
| Loading solution 1-1 | Loaded with loading solution 1-1 | 64 |

Figure 2:
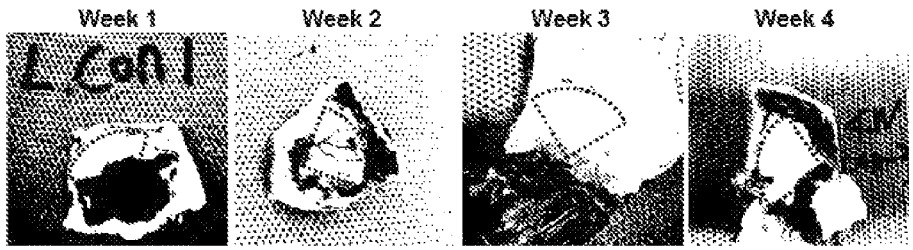
FIG. 2 shows a size change in the dermal layer with time after the dermal layer for grafting is implanted. The grafted acellular dermal matrices did not change in size with time for control 1 in which an acellular dermal matrix had been immersed in PBS (A), control 2 in which an acellular dermal matrix had been immersed in loading solution 1-1 for about 30 min (B), or control 3 in which 0.005% by weight of chitosan had been loaded (C). In contrast, a dermal layer for grafting having a loading solution 1-1 loaded thereto according to the present invention exhibited a behavior similar to those of the controls for three weeks, but became small as the edges of the grafted dermal layer were degraded from week 4 after grafting (D).
Figure 2:
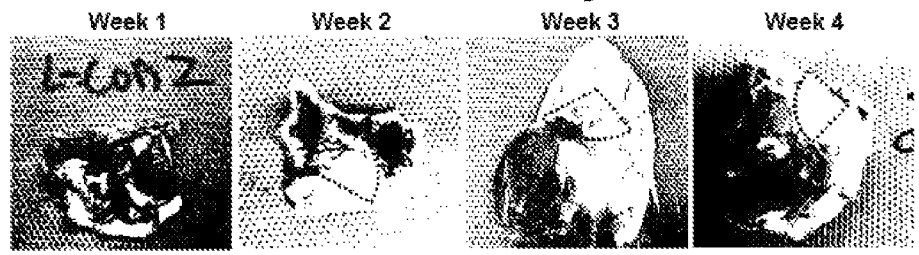
Figure 2:
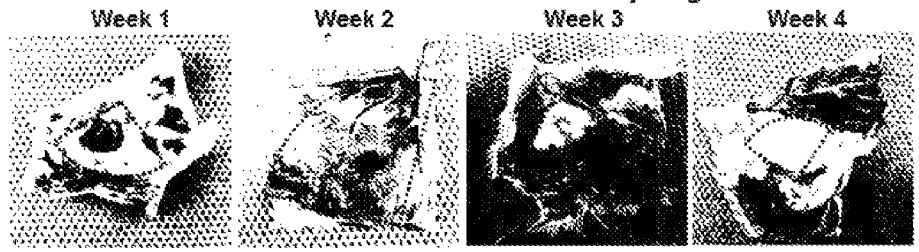
Figure 2:
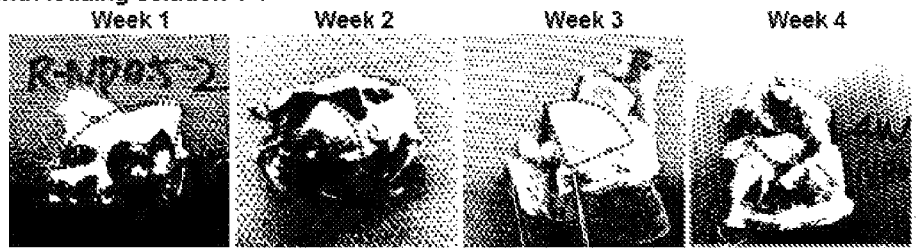

When grafted, as shown in Table 2 and FIG. 2, control 1 (acellular dermal matrix immersed in PBS) (A), control 2 (acellular dermal layer immersed in loading solution 1-1) (B), and control 3 (acellular dermal matrix loaded with 0.005% by weight chitosan) (C) showed almost no change in size with time. In contrast, the dermal layer for grafting according to the present invention did not change in size for three weeks, but became small as the edge of the grafted dermal layer became degraded from week 4 after grafting.

The results indicate that a graft survival rate is not improved in either the case where a loading solution is absorbed to only the surface of an acellular dermal matrix by immersion therein, like control 2, or the case where a matrix is loaded with a solution containing chitosan alone, like control 3. Only the dermal layer for grafting produced by loading an acellular dermal matrix with a loading solution containing a DNA fragment mixture and chitosan exhibited an increased graft survival rate.

Experimental Example 2-3: Identification of Cell Survival Rate and Biocompatibility Through Tissue Staining The dermal layer for grafting according to the present invention that was loaded with loading solution 1-1 in Experimental Example 2-1 and the acellular dermal matrix immersed in PBS (control 1) were grafted. Tissues were harvested on weeks 1 and 4 after grafting and stained with H&E to determine biocompatibility and survival rates.

Figure 3:
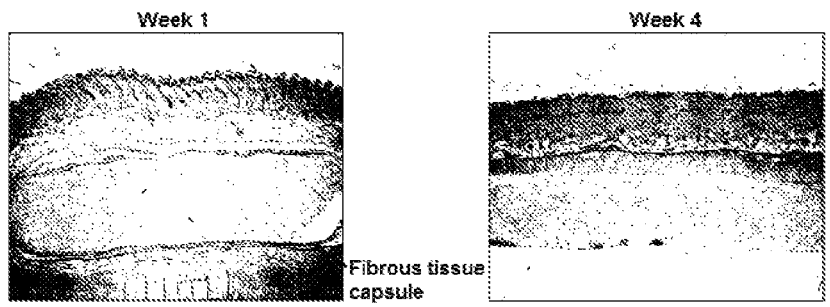
FIG. 3 shows a degree of inflammation induced by the dermal layer for grafting according to the present invention. The implantation of the dermal layer for grafting according to the present invention (B) was observed to cause a reduced initial inflammation reaction, compared to that of control 1 (A), as measured in terms of thicknesses of fibrous tissue capsules induced by inflammation.
Figure 3:
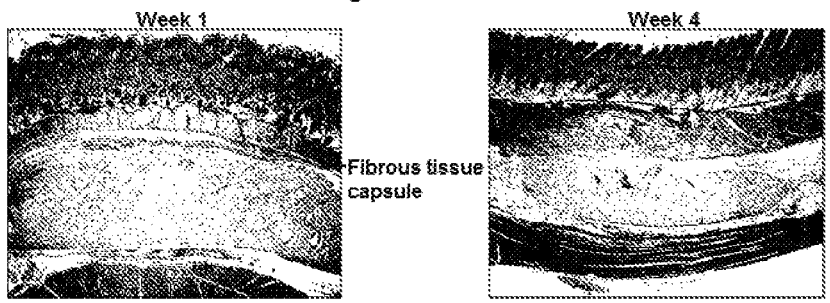
Figure 4:
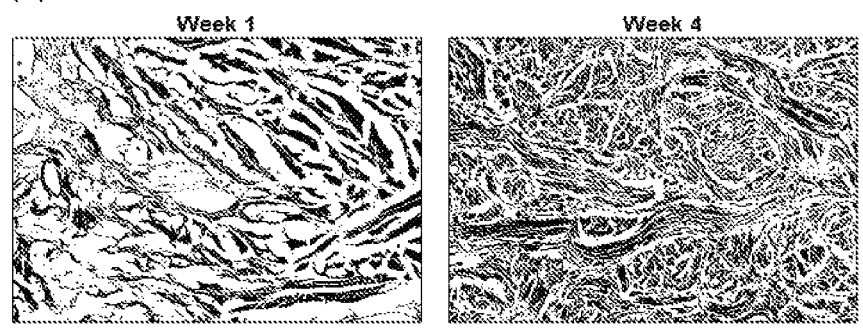
FIG. 4 shows cell survival rates after the implantation of a dermal layer for grafting according to the present invention. A greater population of cells survived upon the implantation of the dermal layer for grafting according to the present invention (B) than control 1 (A).
Figure 4:
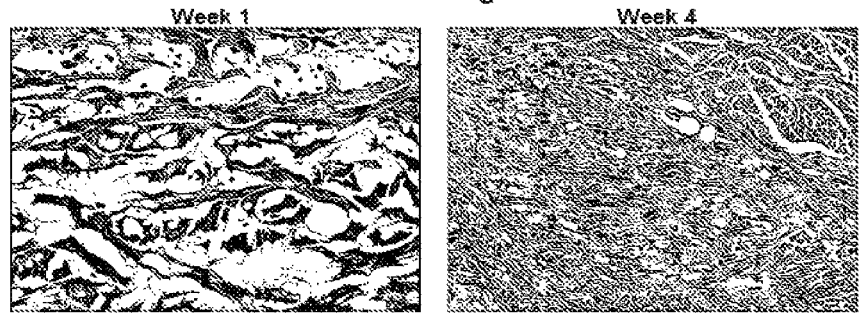

The tissues harvested on weeks 1 and 4 were fixed with formalin, subjected to a series of dehydration, and then embedded in paraffin to construct a paraffin block. The paraffin block was sectioned into 5 μm thick pieces. The tissue pieces were reacted for 1 second with Mayer's hematoxylin solution (Sigma, USA) and washed for 10 min with flowing water. Thereafter, a reaction with an eosin solution (Sigma, USA) was conducted for 3 seconds. After completion of the staining, the tissues were subjected to dehydration and sealed with Permount (Fischer scientific, USA). Histopathological changes of the H&E stained tissue pieces were observed under a microscope and the results are depicted in FIGS. 3 and 4. FIG. 3 shows results of biocompatibility identified by observing fibrous tissue capsules formed by inflammation and FIG. 4 shows results of cell survival rate identified by monitoring the number of cells in the grafted dermal layer.

As shown in FIG. 3, fibrous tissue capsules attributed to inflammation were thin for the dermal layer for grafting according to the present invention (B), compared to control 1 (A), on week 1 after grafting. The fibrous tissue capsules became thin for both control 1 (A) and the dermal layer for grafting according to the present invention (B) on week 4.

For cell survival rates, as shown in FIG. 4, lots of empty spaces were observed among collagens in control 1 (A) and the dermal layer for grafting according to the present invention on week 1 after grafting. In contrast, the empty space was filled with cells on week 4 after grafting. Particularly, a greater population of cells were counted for the dermal layer for grafting according to the present invention (B) than control 1 (A).

From these results, it is understood that the loading solution containing the DNA fragment and chitosan, loaded into the dermal layer for grafting according to the present invention, alleviates initial inflammation and allows cells to rapidly move from adjacent tissues, whereby fusion between the dermal layer and the adjacent tissue can be promoted to increase the cell survival rate.

The invention claimed is:

1. A method for producing a dermal layer for grafting, the method comprising:
    a) preparing a stock solution containing a DNA fragment mixture, wherein the DNA fragment mixture is from fish testis or sperm;
    b) preparing a chitosan stock solution;
    c) mixing the DNA fragment mixture stock solution and the chitosan stock solution in a weight ratio of 20:1-10,000:1 of the DNA fragment mixture to chitosan;
    d) stirring the resulting mixture of the DNA fragment mixture stock solution and the chitosan stock solution;
    e) sterilizing the mixture of the DNA fragment mixture stock solution and the chitosan stock solution to obtain a loading solution; and
    f) loading the loading solution to an acellular dermal matrix to obtain the dermal layer.

2. The method of claim 1, wherein
    in step a, the DNA fragment mixture is dissolved in a buffer at 50° C. to 70° C. for 1 to 3 hours to produce the DNA fragment mixture stock solution;
    in step b, chitosan is dissolved in an acidic buffer to produce the chitosan stock solution;
    in step d the DNA fragment mixture stock solution and the chitosan stock solution are stirred at 65° C. to 75° C. for 1 to 2 hours; and
    in step f, the loading solution is loaded to the acellular dermal matrix by means of a vacuum drug loading device.

3. The method of claim 1, wherein the fish is of the family Salmonidae.

4. The method of claim 1, wherein the DNA fragment mixture has a molecular weight of 50 kDa to 10,000 kDa.

5. The method of claim 1, wherein the DNA fragment mixture is used in an amount of 0.01% by weight to 3% by weight, based on the total weight of the loading solution.

6. The method of claim 1, wherein the chitosan has a molecular weight of 3 kDa to 1,000 kDa.

7. The method of claim 1, wherein the chitosan is used in an amount of $1\times10^{-6}$% by weight to 0.15% by weight, based on the total weight of the loading solution.

8. The method of claim 1, wherein the acellular dermal matrix in step f is a biologically inactivated collagen-based tissue supplement material that has been obtained by removing cells and impurities from a dermal matrix and subjecting the dermal matrix to virus inactivation and then to lyophilization.

9. The method of claim 8, wherein the dermal matrix is an autograft, allograft, or heterograft.

10. The method of claim 1, wherein the loading in step f is carried out by introducing the viscous loading solution into the acellular dermal matrix by means of a pressure to fill empty spaces between collagens.

11. The method of claim 2, wherein the loading solution is loaded into the vacuum drug loading device and the acellular dermal matrix is affixed thereto and wherein the vacuum drug loading device generates a positive or negative pressure to infiltrate the loading solution into empty spaces inside the acellular dermal matrix.

12. The method of claim 2, wherein the chitosan has a molecular weight of 3 kDa to 1,000 kDa.

13. The method of claim 2, wherein the DNA fragment mixture has a molecular weight of 50 kDa to 10,000 kDa.

14. The method of claim 2, wherein the DNA fragment mixture is used in an amount of 0.01% by weight to 3% by weight, based on the total weight of the loading solution.

15. The method of claim 2, wherein the chitosan is used in an amount of $1 \times 10^{-6}$% by weight to 0.15% by weight, based on the total weight of the loading solution.

\* \* \* \* \*